Figure 1:
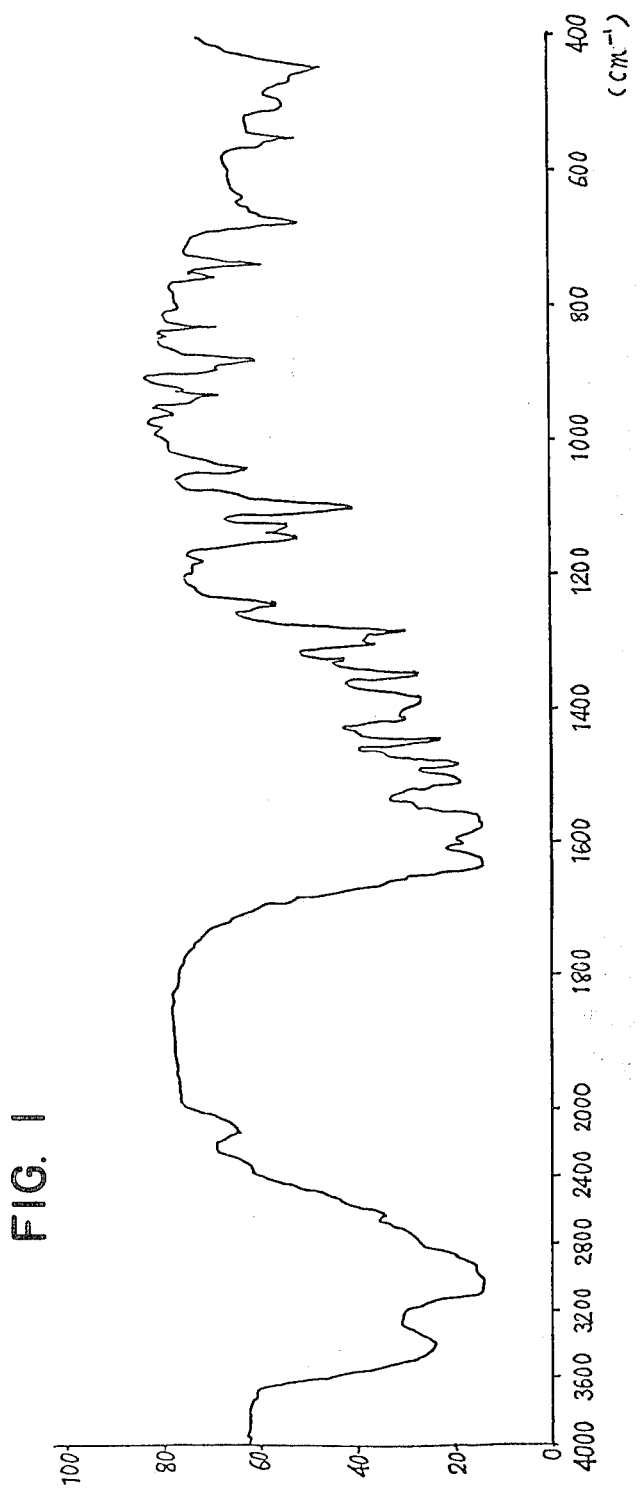

United States Patent [19]

Chibata et al.

[11] 4,420,432

[45] Dec. 13, 1983

[54] CRYSTALLINE SALT OF BASIC L-AMINO ACID WITH L-MALIC ACID AND PROCESS FOR THE PREPARATION THEREOF

[75] Inventors: Ichiro Chibata, Suita; Akihiko Sumi, Ashiya; Hiroshi Ito, Itami; Osamu Ohtsuki, Nagaokakyo; Nozomu Izutsu, Yao, all of Japan

[73] Assignee: Tanabe Seiyaku Co., Ltd., Japan

[21] Appl. No.: 337,320

[22] Filed: Jan. 5, 1982

Related U.S. Application Data

[63] Continuation of Ser. No. 93,810, Nov. 13, 1979, abandoned.

[30] Foreign Application Priority Data

Nov. 20, 1978 [JP] Japan .................................. 53-143603
Apr. 6, 1979 [JP] Japan .................................. 54-42378

[51] Int. Cl.³ ............................................. C07C 101/00
[52] U.S. Cl. .................................................. 260/501.11
[58] Field of Search .................................... 260/501.11

[56] References Cited

U.S. PATENT DOCUMENTS 2,662,046  12/1953  Howe .............................. 260/501.11

FOREIGN PATENT DOCUMENTS 2113774  8/1972  France ............................ 260/501.11

OTHER PUBLICATIONS

Irving, "Evaluation of the Health Aspects of Malic Acid as a Food Ingredient", Life Science Research Office, Bethesda, Md. (1975).
Magalhaes, Chem. Abst., vol. 68, #13347(x) (1968).

*Primary Examiner*—James H. Reamer
*Attorney, Agent, or Firm*—Jordan B. Bierman; Linda Bierman

[57] ABSTRACT

A novel crystalline salt of a basic L-amino acid with L-malic acid, particularly a neutral crystalline salt consisting of 2 moles of L-lysine, L-ornithine or L-arginine with 1 mole of L-malic acid, which have no bitter taste and can be administered by oral route as a nutritive supplement or as a medicine, and further contain no chloride ion and hence are useful for preparing an infusion solution with no undesirable side effect due to chloride ion.

6 Claims, 8 Drawing Figures

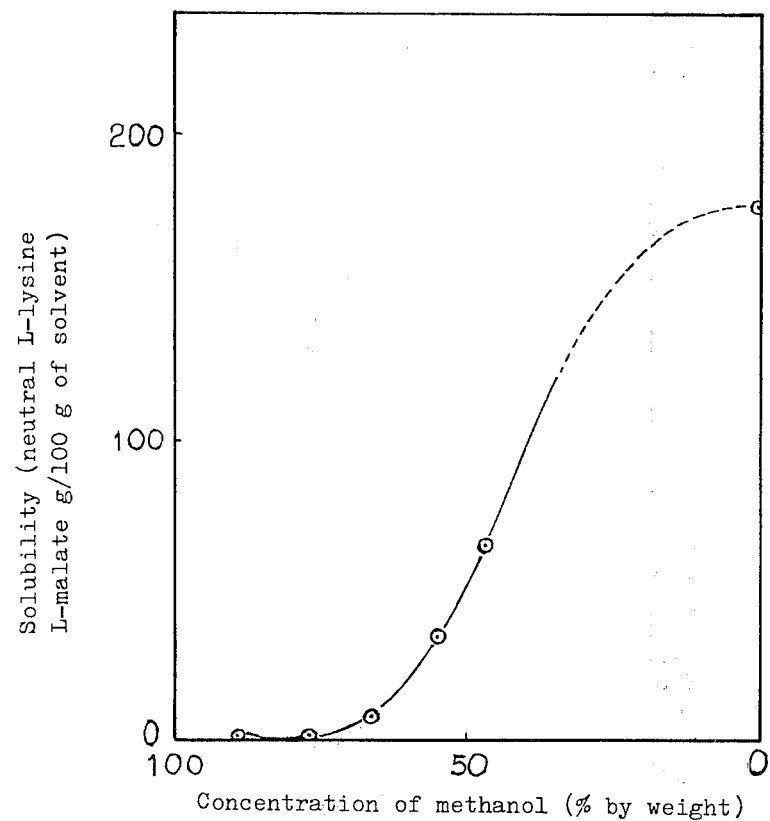

CRYSTALLINE SALT OF BASIC L-AMINO ACID WITH L-MALIC ACID AND PROCESS FOR THE PREPARATION THEREOF

This application is a continuation application of Ser. No. 093,810, filed Nov. 13, 1979 now abandoned, which claims the priority of Japanese Application Nos. 53-143603, filed Nov. 20, 1978 and 54-42378, filed Apr. 6, 1979.

The present invention relates to a novel neutral crystalline salt of a basic L-amino acid such as L-lysine, L-ornithine or L-arginine with L-malic acid and a process for the preparation thereof.

It is well known that the basic L-amino acids such as L-lysine, L-ornithine, L-arginine are useful as a nutritive supplement or as a medicine. However, L-lysine, L-ornithine, etc. are hardly isolated in the form of crystal, and even if they are isolated, they easily absorb carbon dioxide and moisture in air to result in change of their components. Accordingly, they are usually used in the form of hydrochloride salt. When an amino acid solution containing the basic amino acids in the form of hydrochloride salt are intraveneously administered to the patients who can not take foods or other nitrients by oral route, it induces a hyperchloremic metabolic acidosis to the patients. Besides, it is not preferable to administer an infusion solution containing a large amount of chloride ion to patients with renal insufficiency. Accordingly, there has recently increased the demand for an amino acid infusion solution containing no chloride ion.

Besides, even when the amino acids-containing preparations are administered by oral route, the amino acids in the form of hydrochloride salt are not preferable because of significantly bitter taste thereof. Such an undesirable property is particularly seen in the preparations containing basic L-amino acids as the primary component. It is proposed to improve the taste of chemical diets containing amino acid mixture as a sole source of nitrogen by adding thereto various flavors, but the bitter taste owing to the basic L-amino acids has not substantially been removed.

As a result of extensive study of the present inventors in order to obtain crystalline basic L-amino acid derivatives containing no chloride ion, it has been found that a neutral salt of a basic L-amino acid with L-malic acid which is easily metabolized in vivo and has pharmacological properties can be prepared in the crystalline form by reacting the basic L-amino acid with L-malic acid in an aqueous medium in the molar ratio of 2:1 (basic L-amino acid: L-malic acid), and these crystalline salts of a basic L-amino acid with L-malic acid have an excellent moisture-stability and a high solubility in water and are useful as a stable basic L-amino acid derivative for various medical and nutritive utilities.

An object of the present invention is to provide a novel derivative of basic L-amino acids having improved properties. Another object of the invention is to provide a stable, crystalline salt of basic L-amino acid. A further object of the invention is to provide a process for the preparation of the novel derivative of basic L-amino acids. These objects and other objects and advantages of the present invention will be appearant to those skilled in the art from the following description.

The crystalline salts of basic L-amino acids with L-malic acid of the present invention include crystalline neutral salts of basic L-amino acids such as L-ornithine, L-arginine or L-lysine with L-malic acid wherein they are combined in the molar ratio of 2:1, for example, neutral crystalline L-ornithine L-malate dihydrate, neutral crystalline L-arginine L-malate anhydride, and neutral crystalline L-lysine L-malate monohydrate, which are all novel.

These neutral salts are useful for the preparation of amino acid solutions containing little or no chloride ion for parenteral use. It is known that when a conventional amino acid-infusion solution is intravenously administered, undesirable hyperammonemia is occasionally induced, but the salt of a basic L-amino acid with L-malic acid of the present invention can prevent the hyperammonemia because the component L-malic acid has an activity of improving liver function and is useful for prevention of ammonia poisoning. Thus, the salt of a basic L-amino acid with L-malic acid of the present invention is useful as a medicine having the pharmacological activities of L-malic acid and/or as a supplement of basic L-amino acid.

Moreover, the neutral crystalline L-ornithine L-malate dihydrate and L-arginine L-malate anhydride have an excellent activity for ammonia detoxication and an activity for improving liver function, and they dissolve in water at any ratio to give a neutral solution, and hence, they can be used alone as a therapeutic agent for treating hepatic diseases and hyperammonemia. The neutral salt of the present invention has no taste and are odorless. Accordingly, the salts of the present invention are also suitable as a basic L-amino acid derivative for oral administration.

Among the salts of basic L-amino acids with L-malic acid, an acidic salt consisting of 1 mole of L-lysine with 1 mole of L-malic acid is known (cf. Japanese Patent Publication (unexamined) No. 77011/1977.) However, the acidic salt is inferior to the neutral salt of the present invention in the following points. That is, an amino acid infusion solution containing the acidic salt has a higher titratable acidity than that containing the neutral salt of the present invention, and hence an intravenous administration of the solution may induce acidosis due to high titratable acidity. Besides, when the infusion solution containing the acidic salt is neutralized with an alkali in order to lower the titratable acidity, it induces an alkalosis, and further, the infusion solution can not be administered to a patient with renal insufficiency. On the other hand, the neutral salt of the present invention has no such undesirable properties as those of the acidic salt. Moreover, the acidic salt should be used in an amino acid infusion solution in a larger amount than the neutral salt in order to get the same concentration of basic L-amino acid, which results in a high osmotic pressure of the infusion solution, and hence, undesirable osmotic diuresis is induced by administering such an infusion solution having a high osmotic pressure to patients.

The neutral crystalline salt of a basic L-amino acid with L-malic acid can be prepared by subjecting the basic L-amino acid and L-malic acid to a neutralization reaction in an aqueous medium (e.g. water) and crystallizing the resulting neutral salt from the reaction mixture. The reaction can be carried out by dissolving about 0.8 to 1.2 mole, preferably about 1 mole, of L-malic acid in an aqueous solution of 2 moles of a basic L-amino acid and regulating the pH of the solution in the range of 6.0 to 8.5, preferably 6.5 to 7.5. When an excess amount of L-malic acid is used, an acidic salt is undesirably produced together.

The crystallization of the neutral salt from the reaction mixture may be carried out, for example, by adding a hydrophilic organic solvent to the reaction mixture, by adding the reaction mixture to a hydrophilic organic solvent, by adding a seed crystal thereto, or by a combination of these methods (e.g. by adding a hydrophilic organic solvent to the reaction mixture to precipitate a part of the crystals and then adding the resulting mixture containing the precipitated crystals to a hydrophilic organic solvent.) When the reaction mixture alone is concentrated, non-crystalline grease like product is obtained because of the high solubility of the neutral salt in water, and the mother liquor is highly viscous, and hence, the separation of the crystalline salt from the liquid is very difficult. The concentration of the neutral salt in the aqueous mixture is not critical for crystallization of the salt, but it is preferably in the range of about 20 to 80% by weight. When the concentration of the neutral salt is lower than about 20% by weight, a larger amount of a hydrophilic organic solvent is required, and on the other hand, when the concentration is over 80% by weight, the precipitated crystals become unfavorably block-like.

The hydrophilic organic solvent includes a lower alkanol having 1 to 3 carbon atoms (e.g. methanol, ethanol, isopropanol), a lower alkanone of 3 to 5 carbon atoms (e.g. acetone), N,N-dimethylformamide, or the like, which may be used alone or in combination of two or more thereof. The most suitable solvent is determined by the kinds of the neutral salts. The amount of the hydrophilic organic solvent may also vary with the kinds of the neutral salts, but the solvent is used so that the water content of the system for crystallization becomes about 5 to 50% by volume, preferably about 10 to 30% by volume, because when the system for crystallization has a high water content, the crystallization rate of the neutral salt is low and the precipitated crystals may again disslove during the separation of the crystals from the mixture. The crystallization may be carried out at a temperature of about 0° C. to 50° C., but is preferably done at a temperature of about 5° C. to 30° C. in order to increase the yield of the neutral crystalline salt.

The crystallization procedure is explained in more detail below.

In case of the neutral crystalline L-ornithine L-malate dihydrate, the reaction mixture of L-ornithine and L-malic acid is firstly concentrated until the concentration of the produced neutral salt in the reaction mixture becomes about 30 to 70% by weight, and then an appropriate amount of a hydrophilic organic solvent is added to the concentrated mixture to crystallize out the salt. During the crystallization of the salt, the hydrophilic organic solvent is continuously or intermittently added to the system so as to decrease the water content of the system, by which more than 90% of the neutral salt can be crystallized out in the form of dihydrate salt.

In case of neutral crystalline L-arginine L-malate anhydride, the reaction mixture is concentrated until the concentration of the neutral salt in the reaction mixture becomes about 30 to 80% by weight, and thereto are added in appropriated amount of a hydrophilic organic solvent and then seed crystals, or are added seed crystals and then a hydrophilic organic solvent. The seed crystals may usually be used in an amount of about 0.01 to 1% by weight, especially about 0.1% by weight, based on the weight of the neutral salt contained in the system.

In case of neutral crystalline L-lysine L-malate monohydrate, the reaction mixture is concentrated until the concentration of the neutral salt in the reaction mixture becomes about 20 to 70% by weight, and then an appropriate amount of a hydrophilic organic solvent is added to the concentrated mixture, or the concentrated mixture is added to an appropriate amount of a hydrophilic organic solvent.

Alternatively, the crystallization of a neutral salt may be carried out by firstly adding a hydrophilic organic solvent to the concentrated mixture and then adding the resulting mixture to a hydrophilic organic solvent. The hydrophilic organic solvent, it is used in such an amount that the water content of the mixture becomes about 10 to 50% by volume, preferably about 10 to 30% by volume.

The present invention is illustrated by the following Examples but is not limited thereto.

EXAMPLE 1

To an aqueous solution of free L-ornithine (400 ml, content of L-ornithine: 1.167 mole) is gradually added with stirring L-malic acid (78.29 g, ½ mole per 1 mole of L-ornithine). The reaction mixture is concentrated under reduced pressure until the total amount of the mixture becomes 500 g. To the resulting aqueous solution is added with stirring methanol (300 ml), by which a little amount of crystals is precipitated. To the mixture is further added methanol (each 100 ml) five times at an interval of 10 minutes. The mixture is allowed to stand at room temperature to crystallize out the salt well, and the precipitated crystals are separated by filtration. The crystals are washed with a 90% aqueous methanol solution and are air-dried at 60° C. overnight to give neutral L-ornithine L-malate dihydrate (233.5 g, yield: 92.1%) as colorless platy crystal. m.p. 136° C. (decomp.)

Specific rotation $[\alpha]_D^{20} +21.83°$ (c=8, 6 N HCl).

IR spectrum (KBr): It is shown in the accompanying FIG. 1.

Water content of the crystals (i.e. water of crystallization), measured by Karl Fischer method: Calcd: 8.29%, Found: 8.39%.

Elementary Analysis for $(C_5H_{12}NO_2)_2 \cdot C_4H_6O_5 \cdot 2H_2O$: Calcd: C,38.71; H,7.89; N,12.90; O,40.51. Found: C,38.75; H,7.68; N,12.94; O,40.31.

Figure 2:
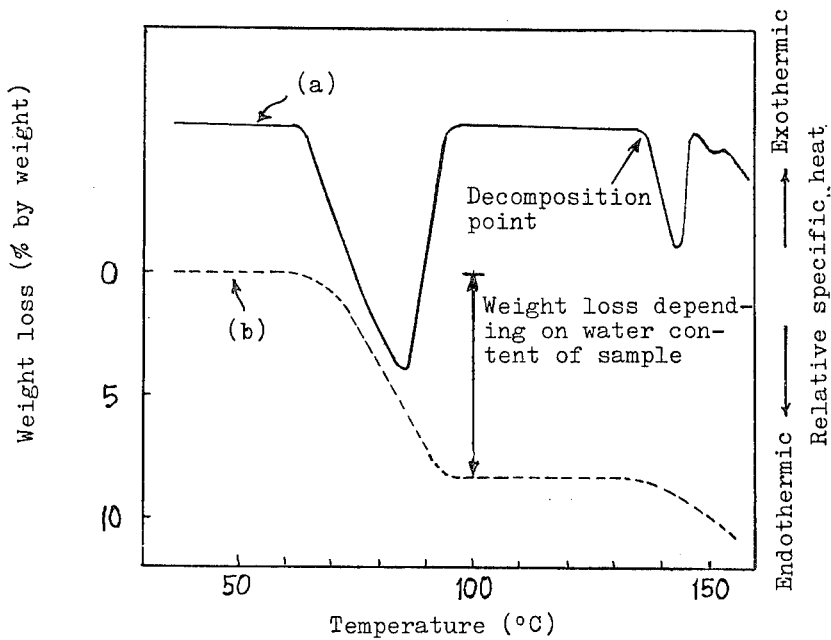

Thermal analysis: The results of a differential thermal analysis (heating rate: 1° C./minute, under nitrogen gas) and of a thermogravimetric analysis are shown in the accompanying FIG. 2. In FIG. 2, (a) is the differential thermal analysis curve, and (b) is the thermogravimetric analysis curve.

Based on the fact that the decrease of weight of the crystals corresponds well to the water content (8.39%) measured by Karl Fischer method and the elementally analysis, it is confirmed that the crystals obtained above is neutral L-ornithine L-malate dihydrate which consists of 2.00 moles of L-ornithine, 1.00 mole of L-malic acid and 2.00 moles of water (i.e. water of crystallization).

Figure 3:
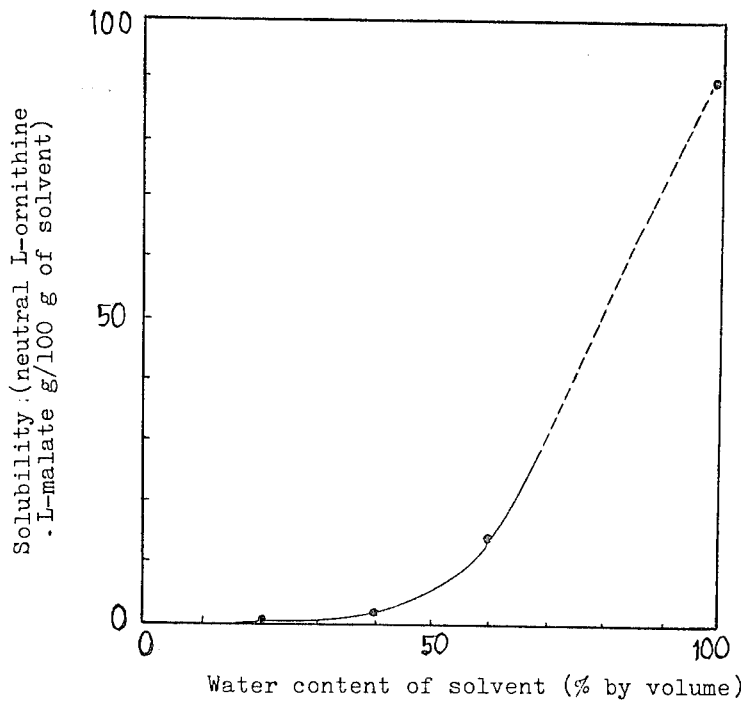

Solubility in aqueous methanol solution (at 10° C.): It is as shown in the accompanying FIG. 3.

pH value of 10% aqueous solution: pH 6.6

Critical relative humidity (at 30° C.): 86% relative humidity (RH)

Figure 4:
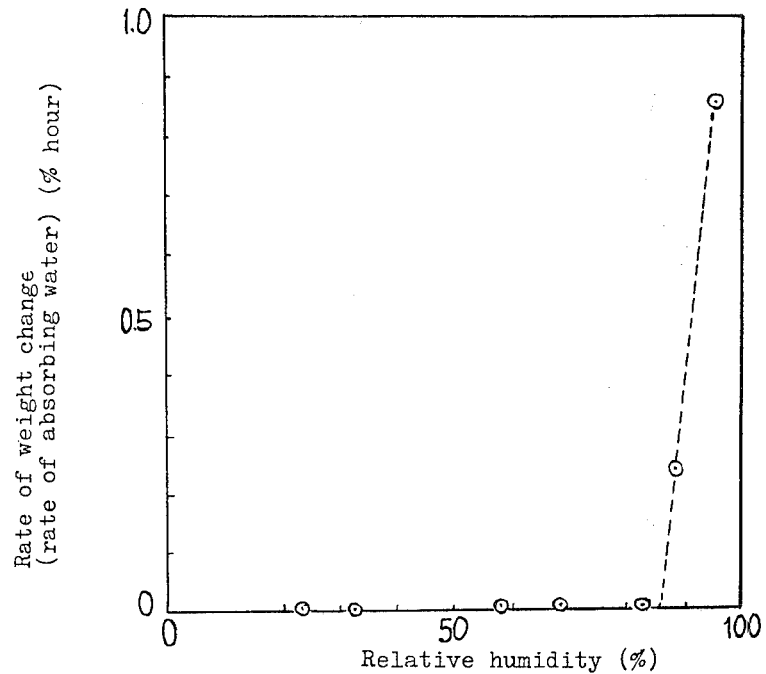

Moisture stability (at 30° C.): It is as shown in the accompanying FIG. 4.

When the crystals obtained above are air-dried at 80° C. overnight, there is obtained neutral L-ornithine L- malate anhydride, but when the anhydrous crystals are allowed to stand in air at room temperature, they absorb moisture corresponding to dihydrate, but thereafter, the amount of the water content thereof is no more varied.

EXAMPLE 2

To an aqueous solution of free L-ornithine [100 ml, content of L-ornithine: 20.23 g(0.15312 mole)] is gradually added with stirring L-malic acid (8.21 g, 0.8 mole per 2 moles of L-ornithine). The reaction mixture is concentrated under reduced pressured until the total amount of the mixture becomes 60 g. To the resulting aqueous solution is added with stirring methanol (30 ml), by which a little amount of crystals is precipitated. After 30 minutes, methanol (20 ml) is further added thereto at room temperature. The resulting mixture is treated in the same manner as described in Example 1 to give neutral L-ornithine L-malate dihydrate (25.0 g, yield: 93.95%) as colorless platy crystal.

The physical and chemcial properties of this product are identical with those of the product obtained in Example 1.

EXAMPLE 3

To an aqueous solution of free L-arginine (content of L-arginine: 0.05 mole) is added L-malic acid (3.35 g, ½ mole per 1 mole of L-arginine) (pH value of the reaction mixture: 7.0). The resulting reaction mixture is concentrated under reduced pressure until the total amount of the mixture becomes 15.2 g, (while the concentrated mixture is allowed to stand at room temperature overnight, no crystal precipitates). To the solution is added methanol (4 ml) and further is added seed crystals of neutral L-arginine DL-malate, and the mixture is allowed to stand overnight. The precipitated crystals are collected by filtration and washed with a 80% aqueous methanol solution and are air-dried at 60° C. overnight to give neutral L-arginine L-malate anhydrate (8.6 g, yield: 71.3%) as colorless granular or prismatic crystal. m.p. 219° C. (decomp.)

Specific rotation $[\alpha]_D +20.94°$ (c=8, 6 N HCl).

Figure 5:
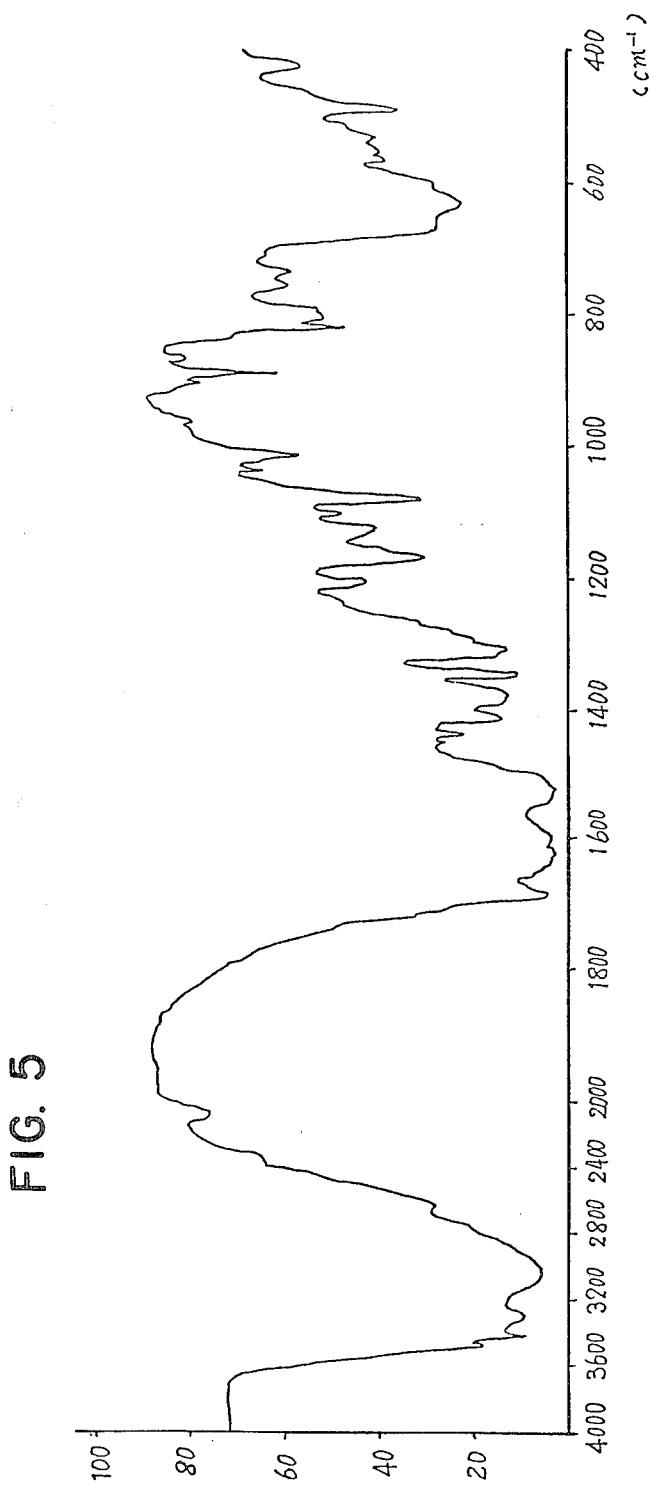

IR spectrum (KBr): It is shown in the accompanying FIG. 5.

Content of L-arginine and L-malic acid: It is shown in the following Table 1.

TABLE 1

|  | Found (%)* | Calculated (%)** |
| --- | --- | --- |
| L-Arginine | 72.15 | 72.21 |
| L-Malic acid | 27.85 | 27.79 |

[Remarks]:
*The content of L-arginine is measured by a titration method with perchloric acid, and the content of L-malic acid is measured by an absorptionmetric method using a 2,7-naphthalenediol reagent.
**It is calculated as $(C_6H_{14}N_4O_4)_2 \cdot C_4H_6O_5$.

Elementary analysis for $C_6H_{14}N_4O_4)_2 \cdot C_4H_6O_5$. Calcd: C,39.83; H,7.10; N,23.23. Found: C,39.85; H,7.12; N,23.21.

Figure 6:
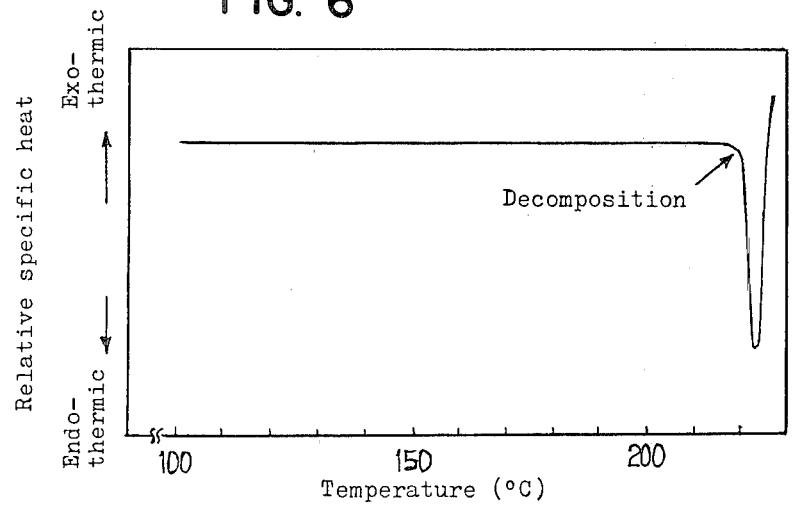

Differential thermal analysis: The results are shown in the accompanying FIG. 6 (heating rate: 1° C./minute, under nitrogen gas).

Solubility in water (at 10° C.): 139.2 (g/100 g of water).

pH value of 10% aqueous solution: pH 7.0.

Critical relative humidity (at 40° C.): 85% RH.

Besides, to an aqueous solution of free L-arginine (content of L-arginine: 0.05 mole) is added DL-malic acid (0.025 mole) (pH value of the solution: 7.0). The solution is concentrated under reduced pressure until the total weight of the mixture becomes 15.2 g. The concentrated mixture is allowed to stanged overnight. The resulting crystals are collected and subjected to chemical analysis. As a result, it is confirmed that the product is crystals of neutral L-arginine L-malate. Yield: 6.7 g, m.p. 220° C.

EXAMPLE 4

L-Arginine hydrochloride (22 g, when converted into L-arginine, 18.2 g) is dissloved in water (800 ml). The solution is passed through a column packed with a strongly acidic iron exchange resin, Amberlite IR-120 (H type, 150 ml). After washing with water (300 ml), the column is eluted with 1 N aqueous ammonia (500 ml). The eluated is concentrated under reduced pressure until the total volume becomes about 40 ml, and thereafter, the concentrated mixture is treated with charcoal and filtered. To the resulting aqueous solution (content of L-arginine: 0.0998 mole) is added L-malic acid (6.62 g) and the mixture is regulated to pH 7.0. The reaction mixture is concentrated under reduced pressure until the total amount of the mixture becomes 34.7 g. To the concentrated mixture is added a seed crystal of a neutral L-arginine L-malate (0.1 g). To the mixture is added with stirring in portions methanol (20 ml) and then the mixture is cooled to 10° C. The precipitated crystals are collected by filtration and washed with 80% aqueous methanol solution and air-dried at 60° C. overnight to give neutral L-arginine L-malate anhydride (23 g, yield: 95.5%) as colorless granular or pillar crystals.

The physical and chemical properties of this product are identical with those of the product obtained in Example 3.

EXAMPLE 5

To an aqueous solution of free L-lysine (200 ml, content of L-lysine: 0.45 mole) is gradually added with stirring L-malic acid (30.16 g, ½ mole per 1 mole of L-ysine). The reaction mixture is concentrated under reduced pressure to give a 50% aqueous solution of neutral L-lysine L-malate (liquid volume: about 170 ml). To the resulting solution is gradually added with stirring methanol (200 ml) to precipitate crystals. To a separate vessel containing methanol (470 ml) is added with stirring the above-obtained mixture, and the mixture is stirred at room temperature for about 4 hours. The precipitated crystals are collected by filtration and washed with methanol and air-dried at 40° C. overnight to give a neutral L-lysine L-malate monohydrate (91.9 g, yield: 92.5%) as colorless needle or prismatic crystals. m.p. 216° C. (decomp.)

Specific rotation $[\alpha]_D^{20} + 19.42°$ (c=8, 6 N HCl).

Figure 7:
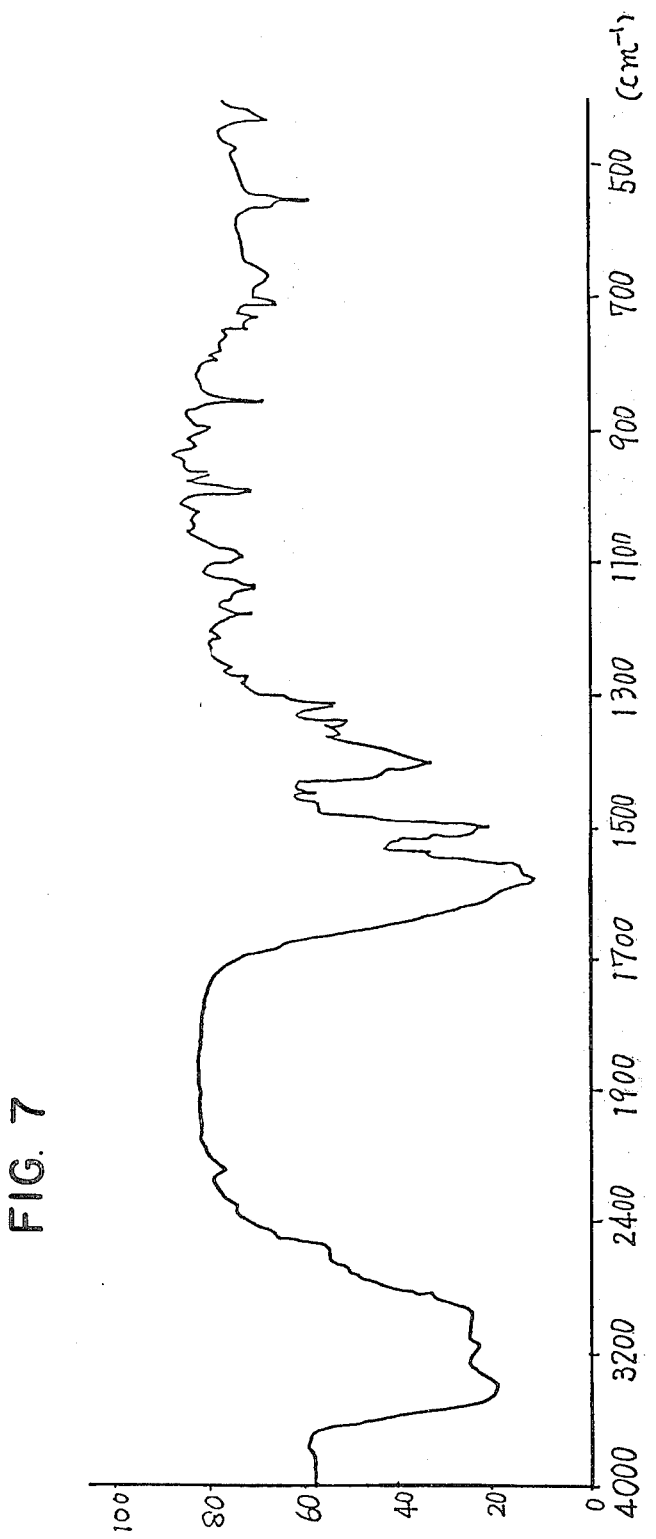

IR spectrum (KBr): It is shown in the accompanaying FIG. 7.

Contents of L-lysine, L-malic acid, and water of crystallization: They are as shown in the following Table 2.

TABLE 2

|  | Found (%)* | Calculated (%)** |
| --- | --- | --- |
| L-Lysine | 65.66 | 65.78 |
| L-Malic acid | 30.22 | 30.17 |
| Water of crys- | 4.12 | 4.05 |

TABLE 2-continued

| | Found (%)* | Calculated (%)** |
|---|---|---|
| tallization | | |

[Remarks]:
*The contents of L-lysine is measured by a titration method with perchloric acid, the content of L-malic acid is measured by the same method as mentioned hereinbefore, and the water content of thereof is measured by Karl Fischer method.
**It is calculated as $(C_6H_{14}N_2O_2)_2 \cdot C_4H_6O_5 \cdot H_2O$ Elementary analysis for $(C_6H_{14}N_2O_2)_2 \cdot C_4H_6O_5 \cdot H_2O$: Calcd: C,43.24; H,8.16; N,12.61. Found: C,43.46; H,8.22; N,12.79.

Thermal analysis: As a result of a differential thermal analysis (heating rate: 10° C./minute, under nitrogen gas) and a thermogravimetric analysis, there are observed an endothermic phenomenon and also loss of weight from 53° C., and at the same temperature, loss of weight is 4.01%. Based on the fact that the loss of weight corresponds well to the water content (4.03%) measured by Karl Fischer method and the elementally analysis, it is confirmed that the crystals obtained above are a neutral L-lysine L-malate monohydrate which consists of 2 moles of L-lysine, 1 mole of L-malic acid and 1 mole of water (i.e. water of crystallization).

Solubility in aqueous methanol solution (at 10° C.): It is as shown in the accompanying FIG. 8.

Solubility in water (at 10° C.): 192.6 (g/100 g of water). pH value of 10% aqueous solution: pH 6.8. Critical relative humidity (at 40° C.): 66% RH.

When the crystals obtained above are air-dried at 65° C. overnight, there is obtained neutral L-lysine L-malate anhydride, but when the anhydrous crystals are allowed to stand in air at room temperature, they absorb moisture corresponding to monohydrate within one hour, and thereafter, the water content thereof is no more varied.

EXAMPLE 6

To an aqueous solution (200 ml) of free L-lysine (content of L-lysine: 0.558 mole) is gradually added with stirring L-malic acid (36.51 g, ½ mole per 1 mole of L-lysine). After the reaction, the reaction mixture is concentrated under reduced pressure until the total amount of the mixture becomes 214 ml. To the resulting aqueous solution is added with stirring methanol (250 ml) to precipitate crystals. To the mixture is further added methanol (each 55 ml) for ten times at an interval of 30 minutes in order to precipitate crystals well. The precipitated crystals are collected by filtration and are treated in the same manner as described in Example 5 to give neutral L-lysine L-malate monohydrate (115.3 g, yield: 95%) as colorless needle or prismatic crystals.

The physical and chemical properties of this product are identical to those of the product obtained in Example 5.

EXAMPLE 7

In the same manner as described in Example 5, there is obtained an aqueous solution (185.3 g) of neutral L-lysine L-malate (concentration of the neutral L-lysine L-malate: 50% by weight). To a stirring vessel containing ethanol (500 ml) is gradually added the solution of neutral L-lysine L-malate obtained above to precipitate crystals well. The precipitated crystals are collected by filtration and air-dried at 40° C. overnight to give neutral L-lysine L-malate monohydrate (94 g, yield: 93.0%).

The physical and chemical properties of this product are identical with those of the product obtained in Example 5.

What is claimed is:

1. A method for preparing a neutral crystalline salt of a basic L-amino acid and L-malic acid which comprises reacting 2 moles of said L-amino acid taken from the class consisting of L-ornithine, L-arginine, and L-lysine with 1 mole of L-malic acid in an aqueous medium, concentrating the reaction mixture until it contains about 20% to about 70% by weight of said neutral salt, mixing the concentrated mixture with a hydrophilic organic solvent taken from the class consisting of an alkanol of 1 to 3 carbon atoms, an alkanone of 3 to 5 carbon atoms, N-N'-dimethylformamide and mixtures thereof, to a water content of the system for crystallization of about 10% to about 30% by volume, crystallizing said neutral salt and recovering said salt from the reaction mixture.

2. The method of claim 1 wherein said L-amino acid is L-lysine.

3. A neutral crystalline salt taken from the class consisting of di-L-lysine L-malate, di-L-ornithine L-malate, and di-L-arginine L-malate.

4. The compound of claim 3 which is di-L-lysine L-malate.

5. A method according to claim 1 wherein the hydrophilic organic solvent is an alkanol of 1 to 3 carbon atoms.

6. A method according to claim 5, wherein the hydrophilic organic solvent is a member selected from the group consisting of methanol and ethanol.

* * * * *